(12) United States Patent
Lee

(10) Patent No.: US 8,974,786 B2
(45) Date of Patent: Mar. 10, 2015

(54) HUMANIZED ANTIBODIES TO CA215

(71) Applicant: Vancouver Biotech Ltd., Vancouver (CA)

(72) Inventor: Gregory Lee, Vancouver (CA)

(73) Assignee: Vancouver Biotech Ltd., Vancouver (CA)

(*) Notice: Subject to any disclaimer, the term of this patent is extended or adjusted under 35 U.S.C. 154(b) by 0 days.

(21) Appl. No.: 13/797,204

(22) Filed: Mar. 12, 2013

(65) Prior Publication Data

US 2013/0340102 A1   Dec. 19, 2013

Related U.S. Application Data

(60) Provisional application No. 61/659,354, filed on Jun. 13, 2012.

(51) Int. Cl.
- *A61K 39/395* (2006.01)
- *C07K 16/30* (2006.01)
- *A61K 45/06* (2006.01)

(52) U.S. Cl.
CPC ............... *C07K 16/30* (2013.01); *A61K 45/06* (2013.01); *A61K 39/39558* (2013.01); *C07K 2317/24* (2013.01); *C07K 2317/33* (2013.01)
USPC .................. 424/133.1; 424/174.1; 530/387.3; 530/387.7

(58) Field of Classification Search
None
See application file for complete search history.

(56) References Cited

U.S. PATENT DOCUMENTS 5,650,291 A    7/1997  Lee
8,143,373 B2 *  3/2012  Lee ............................... 530/300

FOREIGN PATENT DOCUMENTS

WO    WO-2008/138139    11/2008

OTHER PUBLICATIONS

Paul, Fundamental Immunology, 3rd Edition, 1993, pp. 292-295.*
Rudikoff et al (Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
Strome et al., The Oncologist, 2007; 12:1084-95.*
Brand et al., Anticancer Res. 2006; 26:463-70.*
International Search Report and Written Opinion for PCT/IB2013/001834, mailed Dec. 5, 2013, 11 pages.
Lee et al., "Preclinical assessment of anti-cancer drugs by using RP215 monoclonal antibody", Cancer Biology & Therapy (2009) 8(2):161-166.

* cited by examiner

*Primary Examiner* — Sheela J Huff
(74) *Attorney, Agent, or Firm* — Morrison & Foerster LLP

(57) ABSTRACT

Provided herein are humanized forms of murine RP215 monoclonal antibodies and methods of using the same. These humanized RP215 monoclonal antibodies were characterized in terms of their respective affinity and specificity to the corresponding tumor-associated antigen, CA215, and shown to be comparable to those of murine RP215.

17 Claims, 7 Drawing Sheets

Sequence Analysis ($V_L$)

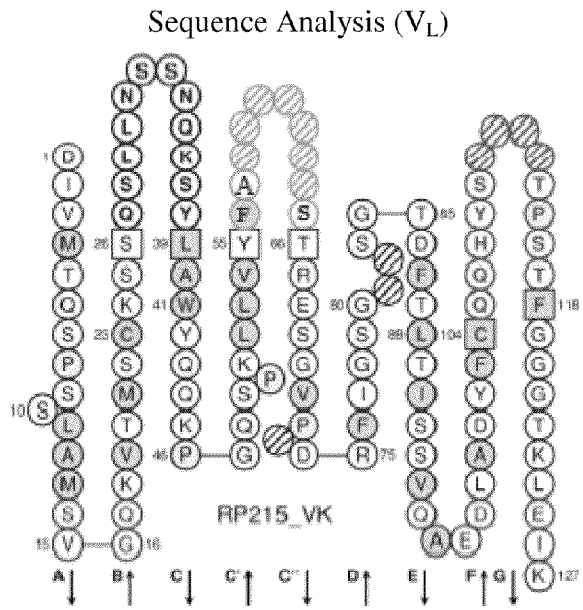

- 3 CDR loops are highlighted in primary structure

DIVMTQSPSSLAMSVGQKVTMSCKSSQSLLNSSNQKSYLAWYQQKPGQSPKLLVFASTRESG
VPDRFIGSGSGTDFTLTISSVQAEDLADYFCQQHYSTPSTFGGGTKLEIK

- Key residues (C-W-C-F) identified
- No free Cys
- No N-linked glycosylation sites

Figure 3

- $V_L$ (Kappa chain) donors
  - Germline donor: IGKV4-1*01 and IGKJ4*01
    DIVMTQSPDSLAVSLGERATINCKSSQSVLYSSNNKNYLAWYQQKPGQPPKLLIYWASTRESGVPDRFSGSGSGTDF
    TLTISSLQAEDVAVYYCQQYYSTP...LTFGGGTKVEIK
  - Rearranged donor: gi|95007535|emb|CAJ57195.1
    DIVMTQSPDSLAVSLGERATINCKSSQSVLYSSNNKNYLAWYQQKPGQPPKLLIYWASTRESGVPDRFSGSGSGTDF
    TLTISSLQAEDVAVYYCQQYYSTPLTFGGGTKLEIK

- $V_H$ donors
  - Germline donor: IGHV1-46*03 and IGHJ1*01
    QVQLVQSGAEVKKPGASVKVSCKASGYTFTSYYMHWVRQAPGQGLEWMGIINPSGGSTSYAQKFQGRVTMTRD
    TSTSTVYMELSSLRSEDTAVYYCAR...AEYFQHWGQGTLVTVSS
  - Rearranged donor: gi|4836322|gb|AAD30405.1|AF115119_1
    QVQLVESGAEVKKPGASVKVSCKASGYTFTSYAINWVRQAPGQGLEWMGGIIPIFGTANYAQKFQGRVTITADEST
    STAYMELSSLRSEDTAVYYCARGAAVAGWGQGTLVTVSS

Figure 4

Heavy chain

```
                   FR1                            CDR1       FR2                   CDR2
hRP215_VH1     QVQLVQSGAEVKKPGASVKVSCKASGYTFT  DYWMH  WVRQAPGQGLEWMG  AIDTSDSYTRY  60
hRP215_VH2     QVQLVESGAEVKKPGASVKVSCKASGYTFT  DYWMH  WVRQAPGQGLEWMG  GIDTSDSYTRY  60
hRP215_VH3     QVQLVQSGAEVKKPGASVKVSCKASGYTFT  DYWMH  WVRQAPGQGLEWIG  AIDTSDSYTRY  60
RP215_Murine   QVQLQQPGAELVMPGASVKMSCKASGYTFT  DYWMH  WVKQRPGQGLEWIG  AIDTSDSYTRY  60
               ****  ***   ******:**********  *****  **:*  *******:*   **********

FR3                            CDR3   JH
hRP215_VH1     AQKFQG  RVTMTVDESTSTVYMELSSLRSEDTAVYYCAR  SIYD  WGQGTLVTVSS  113
hRP215_VH2     AQKFQG  RVTITADESTSTAYMELSSLRSEDTAVYYCAR  SIYD  WGQGTLVTVSS  113
hRP215_VH3     AQKFQG  RVTLTVDESTSTAYMELSSLRSEDTAVYYCAR  SIYD  WGQGTLVTVSS  113
RP215_Murine   NQKFKD  KATLTVDESSSTAFMQLSSLTSEDSAVYYCAR  SIYD  WGQGTLVTVSA  113
               ***:.   :.*:*.***:**.:*:****  ***:*******  ****  **********:
```

Light chain

```
                   FR1                        CDR1              FR2                CDR2
hRP215_VL1     DIVMTQSPDSLAVSLGERATINC  KSSQSLLNSSNQKSYLA  WYQQKPGQPPKLLIY  FASTR  60
hRP215_VL2     DIVMTQSPDSLAVSLGERATINC  KSSQSLLNSSNQKSYLA  WYQQKPGQPPKLLVY  FASTR  60
RP215_Murine   DIVMTQSPSSLAMSVGQKVTMSC   KSSQSLLNSSNQKSYLA  WYQQKPGQSPKLLVY  FASTR  60
               ********.***:*:*::.*:.*   *****************  ********.****:*  *****

FR3                                CDR3         FR4
hRP215_VL1     ES  GVPDRFSGSGSGTDFTLTISSLQAEDVAVYYC  QQHYSTPST  FGGGTKLEIK  113
hRP215_VL2     ES  GVPDRFSGSGSGTDFTLTISSLQAEDVAVYFC  QQHYSTPST  FGGGTKLEIK  113
RP215_Murine   ES  GVPDRFIGSGSGTDFTLTISSVQAEDLADYFC  QQHYSTPST  FGGGTKLEIK  113
               **  ******.*****************:****:*   *********  **********
```

Figure 8

DNA sequences for full length antibody expression constructs hRP215_VH1 — H0021
ATGGAGACCGACACCCTGCTGCTCTGGGTGCTGCTGCTCTGGGTGCCCGGCTCCACCGGACAGGTG
CAGCTGTTCAGAGTGGCGCCGAAGTGAAGAAGCCAGGCGCTTCCGTGAAGGTGAGCTGCAAGGCA
TCAGGCTACACCTTCACTGATTATTGGATGCACTGGGTGAGACAGGCACCCGGTCAGGGGCTCGAA
TGGATGGGCGCCATCGATACTAGCGATTCCTATACCAGATACGCACAGAAGTTTCAGGGAAGAGTT
ACCATGACTGTCGATGAATCTACAAGCACCGTCTACATGGAGCTGAGCAGCCTGCGGTCTGAGGAC
ACCGCTGTTACTACTGTGCCCGCTCCATCTATGATTGGGGTCAAGGAACCTTGGTCACAGTGAGT
TCTGCTAGCACCAAGGGCCCCAGCGTGTTCCCTCTGGCCCCCAGCAGCAAGAGCACCAGCGGCGGA
ACCGCCGCCCTGGGCTGCCTGGTGAAGGACTACTTCCCCGAGCCCGTGACCGTGTCCTGGAACAGC
GGCGCTCTGACCAGCGGAGTGCACACCTTCCCTGCCGTGCTGCAGAGCAGCGGCCTGTACTCCCTG
AGCAGCGTGGTGACCGTGCCCAGCAGCAGCCTGGGCACCCAGACCTACATCTGCAACGTGAACCAC
AAGCCCTCCAACACCAAGGTGGACAAGAAGGTGGAGCCTAAGAGCTGCGACAAGACCCACACCTGC
CCTCCCTGCCCCGCCCCCGAGCTGCTGGGCGGACCCAGCGTGTTCCTGTTCCCTCCCAAGCCCAAG
GACACCCTGATGATCAGCCGCACCCCCGAGGTGACCTGCGTGGTGGTGGACGTGAGCCACGAGGAC
CCCGAGGTGAAGTTCAACTGGTACGTGGACGGCGTGGAGGTGCACAACGCCAAGACCAAGCCTCGG
GAGGAGCAGTACAACTCCACCTACCGCGTGGTGAGCGTGCTGACCGTGCTGCACCAGGACTGGCTG
AACGGCAAGGAGTACAAGTGCAAGGTGAGCAACAAGGCCCTGCCCGCTCCCATCGAGAAGACCATC
AGCAAGGCCAAGGGCCAGCCCCGGGAGCCTCAGGTGTACACCCTGCCCCCCAGCCGCGACGAGCTG
ACCAAGAACCAGGTGAGCCTGACCTGCCTGGTGAAGGGCTTCTACCCCTCCGACATCGCCGTGGAG
TGGGAGAGCAACGGCCAGCCTGAGAACAACTACAAGACCACCCCTCCCGTGCTGGACAGCGACGGC
AGCTTCTTCCTGTACAGCAAGCTGACCGTGGACAAGTCCCGGTGGCAGCAGGGCAACGTGTTCAGC
TGCAGCGTGATGCACGAGGCCCTGCACAACCACTACACCCAGAAGAGCCTGAGCCTGAGCCCCGGA
AAGGATTACAAGGACGACGATGACAAGTAG hRP215_VH2 — H0022
ATGGAGACCGACACCCTGCTGCTCTGGGTGCTGCTGCTCTGGGTGCCCGGCTCCACCGGACAGGTG
CAGCTGTTGAGAGTGGCGCCGAAGTGAAGAAGCCAGGCGCTTCCGTGAAGGTGAGCTGCAAGGCA
TCAGGCTACACCTTCACTGATTATTGGATGCACTGGGTGAGACAGGCACCCGGTCAGGGGCTCGAA
TGGATGGGCGCCATCGATACTAGCGATTCCTATACCAGATACGCACAGAAGTTTCAGGGAAGAGTT
ACCATCACTGCCGATGAATCTACAAGCACCGCCTACATGGAGCTGAGCAGCCTGCGGTCTGAGGAC
ACCGCTGTTACTACTGTGCCCGCTCCATCTATGATTGGGGTCAAGGAACCTTGGTCACAGTGAGT
TCTGCTAGCACCAAGGGCCCCAGCGTGTTCCCTCTGGCCCCCAGCAGCAAGAGCACCAGCGGCGGA
ACCGCCGCCCTGGGCTGCCTGGTGAAGGACTACTTCCCCGAGCCCGTGACCGTGTCCTGGAACAGC
GGCGCTCTGACCAGCGGAGTGCACACCTTCCCTGCCGTGCTGCAGAGCAGCGGCCTGTACTCCCTG
AGCAGCGTGGTGACCGTGCCCAGCAGCAGCCTGGGCACCCAGACCTACATCTGCAACGTGAACCAC
AAGCCCTCCAACACCAAGGTGGACAAGAAGGTGGAGCCTAAGAGCTGCGACAAGACCCACACCTGC
CCTCCCTGCCCCGCCCCCGAGCTGCTGGGCGGACCCAGCGTGTTCCTGTTCCCTCCCAAGCCCAAG
GACACCCTGATGATCAGCCGCACCCCCGAGGTGACCTGCGTGGTGGTGGACGTGAGCCACGAGGAC
CCCGAGGTGAAGTTCAACTGGTACGTGGACGGCGTGGAGGTGCACAACGCCAAGACCAAGCCTCGG
GAGGAGCAGTACAACTCCACCTACCGCGTGGTGAGCGTGCTGACCGTGCTGCACCAGGACTGGCTG
AACGGCAAGGAGTACAAGTGCAAGGTGAGCAACAAGGCCCTGCCCGCTCCCATCGAGAAGACCATC
AGCAAGGCCAAGGGCCAGCCCCGGGAGCCTCAGGTGTACACCCTGCCCCCCAGCCGCGACGAGCTG
ACCAAGAACCAGGTGAGCCTGACCTGCCTGGTGAAGGGCTTCTACCCCTCCGACATCGCCGTGGAG
TGGGAGAGCAACGGCCAGCCTGAGAACAACTACAAGACCACCCCTCCCGTGCTGGACAGCGACGGC
AGCTTCTTCCTGTACAGCAAGCTGACCGTGGACAAGTCCCGGTGGCAGCAGGGCAACGTGTTCAGC
TGCAGCGTGATGCACGAGGCCCTGCACAACCACTACACCCAGAAGAGCCTGAGCCTGAGCCCCGGA
AAGGATTACAAGGACGACGATGACAAGTAG

FIG. 9A hRP215_VH3 - H0023
ATGGAGACCGACACCCTGCTGCTCTGGGTGCTGCTGCTCTGGGTGCCCGGCTCCACCGGACAGGTG
CAGCTTGTTCAGAGTGGCGCCGAAGTGAAGAAGCCAGGCGCTTCCGTGAAGGTGAGCTGCAAGGCA
TCAGGCTACACCTTCACTGATTATTGGATGCACTGGGTGAGACAGGCACCCGGTCAGGGGCTCGAA
TGGATGGGCGCCATCGATACTAGCGATTCCTATACCAGATACGCACAGAAGTTTCAGGGAAGAGTT
ACCCTGACTGTCGATGAATCTACAAGCACCGTCTACATGGAGCTGAGCAGCCTGCGGTCTGAGGAC
ACCGCTGTTTACTACTGTGCCCGCTCCATCTATGATTGGGGTCAAGGAACCTTGGTCACAGTGAGT
TCTGCTAGCACCAAGGGCCCCAGCGTGTTCCCTCTGGCCCCCAGCAGCAAGAGCACCAGCGGCGGA
ACCGCCGCCCTGGGCTGCCTGGTGAAGGACTACTTCCCCGAGCCCGTGACCGTGTCCTGGAACAGC
GGCGCTCTGACCAGCGGAGTGCACACCTTCCCTGCCGTGCTGCAGAGCAGCGGCCTGTACTCCCTG
AGCAGCGTGGTGACCGTGCCCAGCAGCAGCCTGGGCACCCAGACCTACATCTGCAACGTGAACCAC
AAGCCCTCCAACACCAAGGTGGACAAGAAGGTGGAGCCTAAGAGCTGCGACAAGACCCACACCTGC
CCTCCCTGCCCCGCCCCCGAGCTGCTGGGCGGACCCAGCGTGTTCCTGTTCCCTCCCAAGCCCAAG
GACACCCTGATGATCAGCCGCACCCCCGAGGTGACCTGCGTGGTGGTGGACGTGAGCCACGAGGAC
CCCGAGGTGAAGTTCAACTGGTACGTGGACGGCGTGGAGGTGCACAACGCCAAGACCAAGCCTCGG
GAGGAGCAGTACAACTCCACCTACCGCGTGGTGAGCGTGCTGACCGTGCTGCACCAGGACTGGCTG
AACGGCAAGGAGTACAAGTGCAAGGTGAGCAACAAGGCCCTGCCCGCTCCCATCGAGAAGACCATC
AGCAAGGCCAAGGGCCAGCCCCGGGAGCCTCAGGTGTACACCCTGCCCCCCAGCCGCGACGAGCTG
ACCAAGAACCAGGTGAGCCTGACCTGCCTGGTGAAGGGCTTCTACCCCTCCGACATCGCCGTGGAG
TGGGAGAGCAACGGCCAGCCTGAGAACAACTACAAGACCACCCCTCCCGTGCTGGACAGCGACGGC
AGCTTCTTCCTGTACAGCAAGCTGACCGTGGACAAGTCCCGGTGGCAGCAGGGCAACGTGTTCAGC
TGCAGCGTGATGCACGAGGCCCTGCACAACCACTACACCCAGAAGAGCCTGAGCCTGAGCCCCGGA
AAGGATTACAAGGACGACGATGACAAGTAG hRP215_VL1 - L0022
ATGGAGACCGACACCCTGCTGCTCTGGGTGCTGCTGCTCTGGGTGCCCGGCTCCACCGGAGATATC
GTGATGACCCAGTCCCCCGACAGCCTGGCCGTCTCTCTGGGTGAGCGGGCAACCATCAACTGTAAG
TCTAGCCAGTCCCTGTTGAACAGTAGCAATCAAAAGAGCTATCTTGCCTGGTATCAGCAAAAGCCT
GGCCAGCCACCAAAACTGCTTATCTATTTCGCTTCCACTCGGGAAAGCGGTGTACCAGACCGCTTT
TCTGGCTCAGGTTCCGGCACAGACTTTACCTTGACCATTAGCTCCCTTCAGGCAGAGGACGTGGCA
GTCTACTATTGCCAGCAACACTACTCCACTCCATCAACCTTTGGAGGTGGCACAAAACTGGAGATT
AAGCGGACCGTGGCCGCCCCCAGCGTGTTCATCTTCCCTCCCAGCGACGAGCAGCTGAAGTCTGGC
ACCGCCAGCGTGGTGTGCCTGCTGAACAACTTCTACCCCCGCGAGGCCAAGGTGCAGTGGAAGGTG
GACAACGCCCTGCAGAGCGGCAACAGCCAGGAGAGCGTGACCGAGCAGGACTCCAAGGACAGCACC
TACAGCCTGAGCAGCACCCTGACCCTGAGCAAGGCCGACTACGAGAAGCACAAGGTGTACGCCTGC
GAGGTGACCCACCAGGGACTGTCTAGCCCCGTGACCAAGAGCTTCAACCGGGGCGAGTGCTAA hRP215_VL2 - L0023
ATGGAGACCGACACCCTGCTGCTCTGGGTGCTGCTGCTCTGGGTGCCCGGCTCCACCGGAGATATC
GTGATGACCCAGTCCCCCGACAGCCTGGCCGTCTCTCTGGGTGAGCGGGCAACCATCAACTGTAAG
TCTAGCCAGTCCCTGTTGAACAGTAGCAATCAAAAGAGCTATCTTGCCTGGTATCAGCAAAAGCCT
GGCCAGCCACCAAAACTGCTTGTCTATTTCGCTTCCACTCGGGAAAGCGGTGTACCAGACCGCTTT
TCTGGCTCAGGTTCCGGCACAGACTTTACCTTGACCATTAGCTCCCTTCAGGCAGAGGACGTGGCA
GTCTACTTTTGCCAGCAACACTACTCCACTCCATCAACCTTTGGAGGTGGCACAAAACTGGAGATT
AAGCGGACCGTGGCCGCCCCCAGCGTGTTCATCTTCCCTCCCAGCGACGAGCAGCTGAAGTCTGGC
ACCGCCAGCGTGGTGTGCCTGCTGAACAACTTCTACCCCCGCGAGGCCAAGGTGCAGTGGAAGGTG
GACAACGCCCTGCAGAGCGGCAACAGCCAGGAGAGCGTGACCGAGCAGGACTCCAAGGACAGCACC
TACAGCCTGAGCAGCACCCTGACCCTGAGCAAGGCCGACTACGAGAAGCACAAGGTGTACGCCTGC
GAGGTGACCCACCAGGGACTGTCTAGCCCCGTGACCAAGAGCTTCAACCGGGGCGAGTGCTAA

HUMANIZED ANTIBODIES TO CA215

CROSS-REFERENCE TO RELATED APPLICATIONS

This application claims priority of U.S. Ser. No. 61/659,354 filed 13 Jun. 2012. The contents of these documents are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 616342000500SeqList.txt, date recorded: Jun. 19, 2013, size: 38,859 bytes).

TECHNICAL FIELD

The invention relates to the field of humanization of RP215 monoclonal antibody which is of murine origin. RP215 is known to recognize specifically a carbohydrate-associated epitope of cancer cell-expressed glycoproteins, known as CA215. The primary structure of the humanized forms of RP215 can then be utilized for the therapeutic treatment of human cancers as antibody-based anticancer drugs.

BACKGROUND ART

RP215 monoclonal antibody described in U.S. Pat. No. 5,650,291 and PCT publication WO2008/138,139 is one of three thousand monoclonal antibodies which were generated in mice immunized against the extract of OC-3-VGH ovarian cancer cell. Through years of effort, it was documented that RP215 reacts specifically with cancer cell-expressed pan cancer biomarker or glycoproteins, designated as CA215. The amino acid sequence of the variable regions of RP215 is disclosed in the PCT publication. The contents of these documents as related to uses for antibodies that bind to CA215 are incorporated herein by reference.

Following comprehensive analysis of more than 100 CA215-derived tryptic peptides by MALDI-TOF MS, it was further demonstrated that CA215 is a mixture of glycoproteins expressed by cancer cells, each of which contains an RP215-specific carbohydrate-associated epitope. Among these glycoproteins are mainly immunoglobulin superfamily (IgSF) proteins including immunoglobulin heavy chains, T cell receptors and cell adhesion molecules as well as mucins and others.

Both in vitro and in vivo biochemical and immunological assays were performed to document that RP215 reacts with the surface of almost all of cancer cells or cancerous tissues in humans. Besides immunohistochemical studies, apoptosis as well as complement-dependent cytotoxicity can be induced to cancer cells in the presence of RP215 at concentrations on the order of µg/ml. Growth inhibition of implanted tumor cells in model systems by RP215 was also demonstrated in nude mouse experiments. In addition, rat anti-idiotypic (Aid) monoclonal antibodies against RP215 were generated. The Ab3 response upon immunizations of these Aid monoclonal antibodies in mice was successfully induced. The anti-aid (Ab3) anti-sera were shown to be functionally equivalent to RP215. Aid monoclonal antibodies may also be used for the development of anti-cancer vaccines for human applications.

To develop RP215-based anti-cancer drugs for human application, it is essential to modify the original murine RP215 monoclonal antibody into humanized form.

DISCLOSURE OF THE INVENTION

The invention is directed to the humanized forms of RP215 monoclonal antibody. The humanized versions of RP215 of the invention were shown to have affinity and specificity to CA215 comparable to, or equivalent to, those of original murine RP215. Thus, in one aspect, the invention is directed to humanized antibodies or fragments that bind CA215 with specificities and affinities substantially equivalent to that of RP215. In particular, the antibodies or fragments with variable regions shown in FIG. 8 are part of the invention.

For complete antibodies of the invention, it is preferred that the constant region of the heavy chain be IgG and the constant region of the light chain be kappa. However, other Ig forms, including IgM, for example, are included as well as those embodiments that have lambda constant regions in their light chains.

In still other aspects, the invention is directed to methods to use the antibodies of the invention in the treatment of cancer in human subjects.

BRIEF DESCRIPTION OF THE DRAWINGS

FIG. 3 (SEQ ID NO:8) shows sequence analysis of VL: 3CDR of murine RP215 loops which are highlighted in primary amino acid sequence with key residues (C-W-C-F) identified and with no free Cys and N-linked glycosylation sites.

FIG. 4 (SEQ ID NOS:9-12) shows human framework donors considered

FIG. 8 (SEQ ID NOS:24-30) shows comparison of amino acid sequences of heavy chain and light chain of humanized forms of RP215 with those of murine RP215.

FIG. 9 (SEQ ID NOS:31-35) shows the nucleotide sequences that encode the amino acid sequences of FIG. 8.

FIG. 9A-B show the nucleotide sequences that encode the amino acid sequences of FIG. 8.

MODES OF CARRYING OUT THE INVENTION

Figure 1:
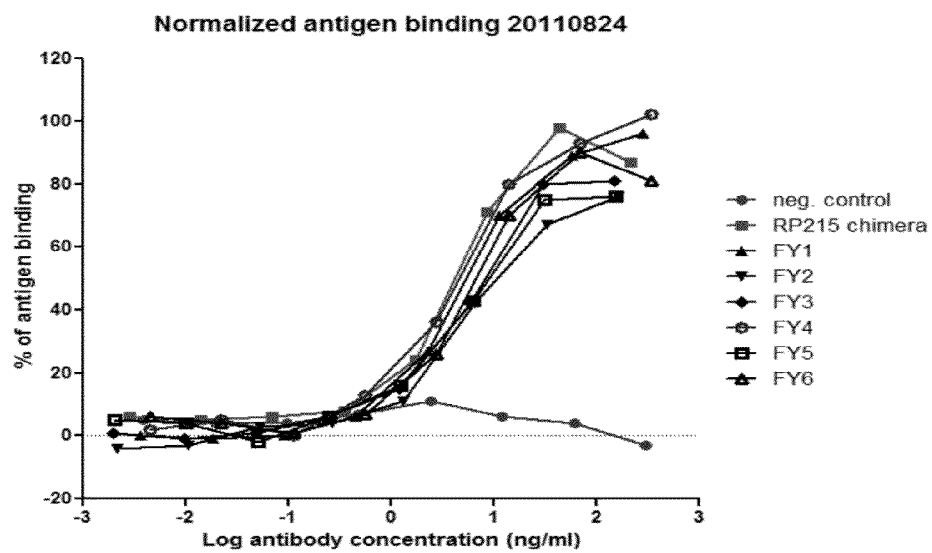
FIG. 1 shows antigen binding curves of various humanized and chimeric forms of RP215 monoclonal antibodies.

The humanized antibodies of the present invention may be in a variety of forms—including whole antibodies, fragments that are immunoreactive with CA215, including Fab, Fab', and F(ab')$_2$ fragments as well as recombinantly produced single-chain antibodies. The resulting humanized forms as noted below are of equivalent affinity and specificity to the murine RP215 and contain substantially similar or identical CDR regions.

The CDR regions of the variable region of both heavy and light chains can be determined by a number of art-known methods, including the numbering system of Kabat which defines, in the light chain CDR1 as residues 24-34, CDR2 as residues 50-56, CDR3 as residues 89-97 and in the heavy chain CDR1 as residues 31-35, CDR2 as residues 50-65 and CDR3 as residues 95-102 (Wu, T. T., and Kabat, E. A., *Exp. Med.* (1970) 132:211-250). CDRs can also be determined according to the system of Clothia which gives slightly different results (Clothia, C., et al., *Nature* (1989) 342:877-883; Al-Laziken, et al., *J. Mol. Biol.* (1997) 273:927-948). Various subsequent authors have suggested some minor modifications. The CDRs as assigned by both Kabat and Clothia systems are included within the scope of the present invention.

Sandwich and/or binding immunoassays were used to demonstrate the substantial equivalence between the humanized forms and murine RP215. Their respective affinity and specificity to the cognate antigen, the cancer cell-expressed CA215, are two important parameters to establish their substantial equivalence.

General Approach for Humanization

Based on the published sequence of the RP215 variable chain, it was determined that five of the CDRs (excluding H3) fall into one of the canonical structure classes indicated as follows:

| CDR | L1 | L2 | L3 | H1 | H2 |
|---|---|---|---|---|---|
| Canonical Structure class | 3/17A | 1/7A | 1/9A | 1/10A | 2/10A |

Human framework donor selection was made through a search of germline followed by rearrangement of human IgG data base using VL and VH sequences with or without CDRs. To obtain human IgG results, normally, we go through each hit to eliminate inappropriate donors (such as mouse sequence or humanized sequence, etc.). For VL and VH sequences, the best hits in each group were aligned. Finally, one germline FR donor and one rearranged (mature) FR donor based on sequence similarity and other factors are selected. These factors included CDR length (except for CDR-H3), CDR canonical structure, proline residues at key positions or factors which may affect proper folding of humanized antibody.

Homology modeling was used to obtain template antibody structure by searching the PDB data base for the template antibody VL and VH sequences with or without CDR. The following conditions are taken into consideration:

(1) Sequence homology
(2) CDR length
(3) CDR canonical structure, and
(4) Model with correct disulfide linkage The antigen binding region of the antibody structure model can then be optimized through the CDR loop data base and canonical structure class as well as comparison to the template structure.

Structural modeling was used to identify residues outside of the CDR loops that might affect CDR configurations. The following binding or interaction factors should be taken into consideration: hydrogen bonding, steric hindrance and other interactions to main chain and side chains of CDR residues.

Back mutation was performed to those residues that are predicted to significantly affect CDR loop structure. Other critical residues were also verified including those in (1) the heterodimer interface in FR donors for proper VL and VH interactions, (2) the intra-chain domain interface and (3) direct interactions to antigen/epitopes in the known structure.

Therefore, based on the above considerations, combinations of different back mutations were designed to balance the minimal need of such process. As a result, low immunogenicity to humans can be obtained and the maximal preservations of antigen-binding affinity can be preserved.

The following examples are offered to illustrate but not to limit the invention.

EXAMPLE 1

Characterization of Humanized RP215 Monoclonal Antibodies

Humanized RP215 monoclonal antibodies with heavy and light chains designated 0021-0023 (VH1-VH3 and VL1-VL2) and the parent murine chains 0024 were generated, expressed and affinity-purified. Various heavy chain/light chain combinations were used to construct antibodies FY1-FY6 as shown in Table 1. ChRP215 is a murine chimera with human IgG.

TABLE 1

|  | VL1 | VL2 | L0024 |
|---|---|---|---|
| VH1 | FY1 | FY4 |  |
| VH2 | FY2 | FY5 |  |
| VH3 | FY3 | FY6 |  |
| H0024 |  |  | ChRP215 |

The titers and amounts of FY1-FY6 from CHO cells are shown in Table 2.

TABLE 2

| Name of antibody | Apparent titer (ng/ml) | Production yield (N = 1) |
|---|---|---|
| Neg. control | NA | 305 |
| RP215 chimera (with human IgG) | 4.2 | 219 |
| FY1 | 5.7 | 287 |
| FY2 | 13.1 | 166 |
| FY3 | 8.4 | 152 |
| FY4 | 4.4 | 351 |
| FY5 | 9.6 | 158 |
| FY6 | 7.1 | 350 |

Binding immunoassays were performed using affinity-purified CA215 coated on microwells, to determine the binding affinities of these humanized RP215 to CA215 and to compare with that of the original murine RP215. The results of such comparative binding assays are presented in FIG. 1. As shown, all of FY1-FY6 have comparable affinities to RP215.

Figure 2:
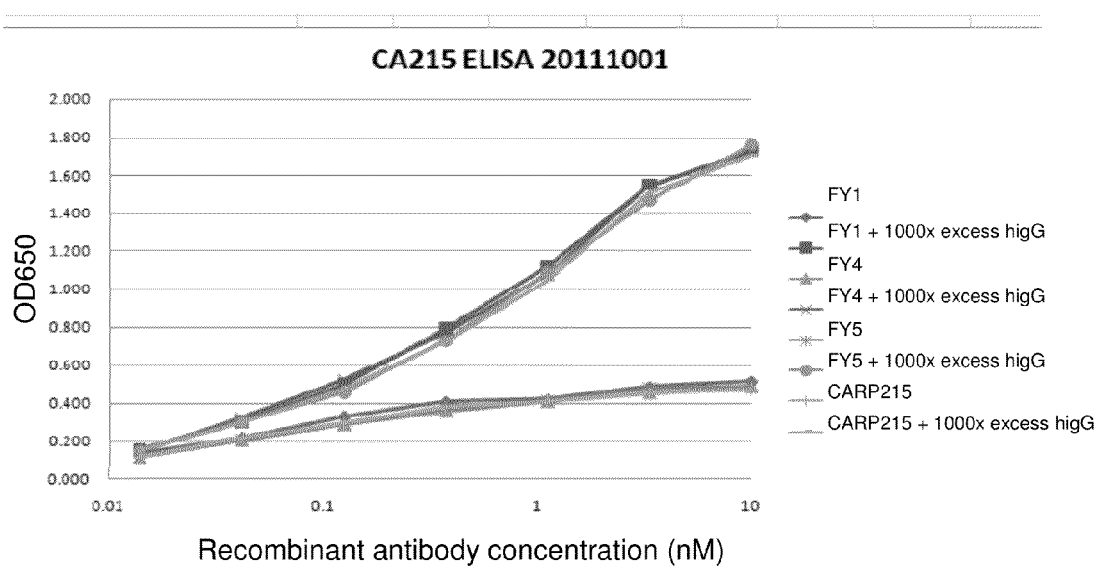
FIG. 2 shows the results of an ELISA to determine the low cross-reactivity of various humanized RP215 monoclonal antibodies to human IgG.
Figure 5:
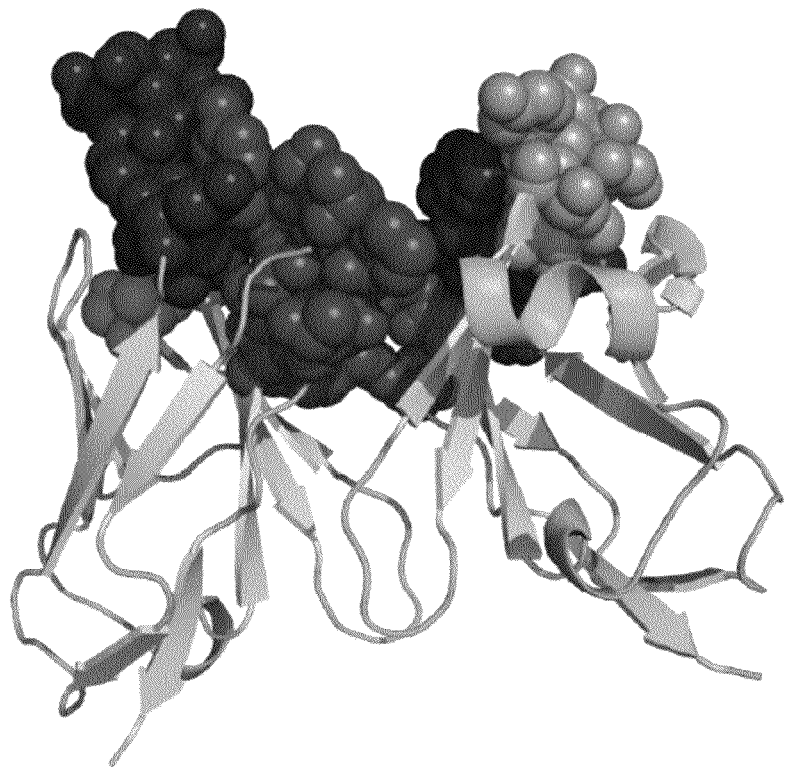
FIG. 5 is a template antibody structure model of murine RP215 (VL shown on left-hand side, VH on right-hand side, and CDR loops shown as spheres with van der Waals radii).
Figure 6:
FIG. 6 is a template antibody structure model of murine RP215. Residues in close proximity to CDR loops are shown as sticks. These residue positions are candidates for back-mutation.
Figure 7:
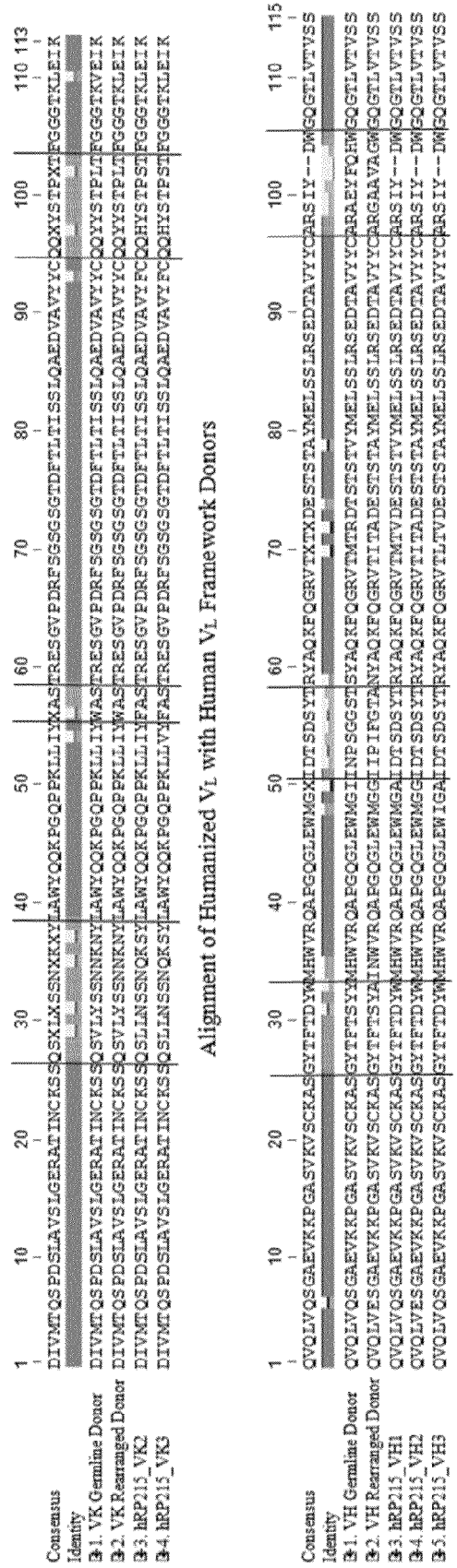
FIG. 7 (SEQ ID NOS:13-23) shows humanized sequences that exhibit high homology to human antibody sequences. hRP215_VH1 has ~97% sequence identity to its closest human FR donor (germline) outside of CDR regions hRP215 ~99% identity to germline FR Alignment of Humanized VH with Human VH Framework Donors regions, while hRP215_VH2 has donor outside of CDRs. Different residues are mostly located within or adjacent to CDRs, with the exception of Loop 3 in VH.

Previously, RP215 was established to have no cross-reactivity to normal human IgG. It reacts only with CA215 expressed by cancer cells that contain RP215-specific carbohydrate-associated epitope. Therefore, the humanized RP215 monoclonal antibodies should also show no cross-reactivity to normal human IgG. This lack-of-cross reactivity result was demonstrated, as humanized RP215 FY1, FY4 and FY5 (similar to the murine chimera) revealed no binding to human IgG as shown in FIG. 2.

FIG. 8 shows the complete amino acid sequences of both heavy and light chains of the humanized antibodies. The complete nucleotide sequences for these chains is shown in FIG. 9.

As a matter of interest, FIGS. 3-7 show various additional structural features of these antibodies.

The invention claimed is:

1. A humanized monoclonal antibody (mAb) or fragment thereof that reacts specifically with a CA215, and that binds to the CA215 with an affinity substantially equivalent to that of RP215, which mAb comprises the CDR regions inherent in one of the heavy chain variable regions set forth in SEQ ID NOS:24-26 and in one of the light chain variable regions set forth in SEQ ID NO:28 or 29 according to the numbering system of either Kabat or Clothia.

2. The mAb or fragment of claim 1, wherein:
   a) the CDR1 region of the heavy chain is DYWMH (SEQ ID NO:1); and
   b) the CDR2 region of the heavy chain is AIDTSD-SYTRYAQKFQG (SEQ ID NO:2) or GIDTSD-SYTRYAQKFQG (SEQ ID NO:3); and
   c) the CDR3 region of the heavy chain is SIYD (SEQ ID NO:4); and
   d) the CDR1 region of the light chain is KSSQSLLNSSN-QKSYLA (SEQ ID NO:5); and
   e) the CDR2 region of the light chain is FASTRES (SEQ ID NO:6); and
   f) the CDR3 region of light chain is QGHYSTPST (SEQ ID NO:7).

3. An mAb or fragment which comprises the variable regions of VH1 (SEQ ID NO:24)+VL1 (SEQ ID NO:28); VH1 (SEQ ID NO:24)+VL2 (SEQ ID NO:29); VH2 (SEQ ID NO:25)+VL1 (SEQ ID NO:28); VH2 (SEQ ID NO:25)+VL2 (SEQ ID NO:29); VH3 (SEQ ID NO:26)+VL1 (SEQ ID NO:28); or VH3 (SEQ ID NO:26)+VL2 (SEQ ID NO:29).

4. The mAb of claim 1 which is a complete antibody.

5. The fragment of claim 1 which is a single-chain antibody.

6. The mAb or fragment of claim 1, coupled to a detectable marker and/or a therapeutic agent.

7. A pharmaceutical composition comprising the mAb or fragment of claim 1 and a pharmaceutically acceptable excipient.

8. The pharmaceutical composition of claim 7 further comprising an additional therapeutic agent.

9. A method to treat a subject for cancer that expresses CA215 which method comprises administering to said subject a composition comprising an mAb or fragment of claim 1.

10. The method of claim 9, wherein the cancer is of the breast, ovary, endometrium, prostate, cervix, pancreas, colon, lung, liver or kidney.

11. The mAb of claim 3 which is a complete antibody.

12. The fragment of claim 3 which is a single-chain antibody.

13. The mAb or fragment of claim 3, coupled to a detectable marker and/or a therapeutic agent.

14. A pharmaceutical composition comprising the mAb or fragment of claim 3 and a pharmaceutically acceptable excipient.

15. The pharmaceutical composition of claim 14 further comprising an additional therapeutic agent.

16. A method to treat a subject for cancer that expresses CA215 which method comprises administering to said subject a composition comprising an mAb or fragment of claim 9.

17. The method of claim 16, wherein the cancer is of the breast, ovary, endometrium, prostate, cervix, pancreas, colon, lung, liver or kidney.

* * * * *

SEQUENCE LISTING

```
<160> NUMBER OF SEQ ID NOS: 35

<210> SEQ ID NO 1
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(5)
<223> OTHER INFORMATION: CDR1 region of hRP215 heavy chain

<400> SEQUENCE: 1

Asp Tyr Trp Met His
1               5

<210> SEQ ID NO 2
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(17)
<223> OTHER INFORMATION: CDR2 region of hRP215 heavy chain

<400> SEQUENCE: 2

Ala Ile Asp Thr Ser Asp Ser Tyr Thr Arg Tyr Ala Gln Lys Phe Gln
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(17)
<223> OTHER INFORMATION: CDR2 region of hRP215 heavy chain

<400> SEQUENCE: 3

Gly Ile Asp Thr Ser Asp Ser Tyr Thr Arg Tyr Ala Gln Lys Phe Gln
1               5                   10                  15

Gly

<210> SEQ ID NO 4
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(4)
```

```
<223> OTHER INFORMATION: CDR3 region of hRP215 heavy chain

<400> SEQUENCE: 4

Ser Ile Tyr Asp
  1

<210> SEQ ID NO 5
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(17)
<223> OTHER INFORMATION: CDR1 region of hRP215 light chain

<400> SEQUENCE: 5

Lys Ser Ser Gln Ser Leu Leu Asn Ser Ser Asn Gln Lys Ser Tyr Leu
  1               5                  10                  15

Ala

<210> SEQ ID NO 6
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(7)
<223> OTHER INFORMATION: CDR2 region of hRP215 light chain

<400> SEQUENCE: 6

Phe Ala Ser Thr Arg Glu Ser
  1               5

<210> SEQ ID NO 7
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(9)
<223> OTHER INFORMATION: CDR3 region of hRP215 light chain

<400> SEQUENCE: 7

Gln Gly His Tyr Ser Thr Pro Ser Thr
  1               5

<210> SEQ ID NO 8
<211> LENGTH: 113
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(113)
<223> OTHER INFORMATION: light chain RP215_murine

<400> SEQUENCE: 8

Asp Ile Val Met Thr Gln Ser Pro Ser Ser Leu Ala Met Ser Val Gly
  1               5                  10                  15

Gln Lys Val Thr Met Ser Cys Lys Ser Ser Gln Ser Leu Leu Asn Ser
                 20                  25                  30
```

Ser Asn Gln Lys Ser Tyr Leu Ala Trp Tyr Gln Gln Lys Pro Gly Gln
            35                  40                  45

Ser Pro Lys Leu Leu Val Tyr Phe Ala Ser Thr Arg Glu Ser Gly Val
 50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys Gln Gln
                 85                  90                  95

His Tyr Ser Thr Pro Ser Thr Phe Gly Gly Gly Thr Lys Leu Glu Ile
            100                 105                 110

Lys

<210> SEQ ID NO 9
<211> LENGTH: 113
<212> TYPE: PRT
<213> ORGANISM: Homo sapiens
<220> FEATURE:
<221> NAME/KEY: CHAIN
<222> LOCATION: (1)...(113)
<223> OTHER INFORMATION: kappa chain germline donor

<400> SEQUENCE: 9

Asp Ile Val Met Thr Gln Ser Pro Asp Ser Leu Ala Val Ser Leu Gly
 1                   5                  10                  15

Glu Arg Ala Thr Ile Asn Cys Lys Ser Ser Gln Ser Val Leu Tyr Ser
                 20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Leu Thr Phe Gly Gly Gly Thr Lys Val Glu Ile
            100                 105                 110

Lys

<210> SEQ ID NO 10
<211> LENGTH: 114
<212> TYPE: PRT
<213> ORGANISM: Homo sapiens
<220> FEATURE:
<221> NAME/KEY: CHAIN
<222> LOCATION: (1)...(114)
<223> OTHER INFORMATION: kappa chain rearranged donor

<400> SEQUENCE: 10

Asp Ile Val Met Thr Gln Ser Pro Asp Ser Leu Ala Val Ser Leu Gly
 1                   5                  10                  15

Glu Arg Ala Thr Ile Asn Cys Lys Ser Ser Gln Ser Val Leu Tyr Ser
                 20                  25                  30

Ser Asn Asn Lys Asn Tyr Leu Ala Trp Tyr Gln Gln Lys Pro Gly
            35                  40                  45

Gln Pro Pro Lys Leu Leu Ile Tyr Trp Ala Ser Thr Arg Glu Ser Gly
 50                  55                  60

Val Pro Asp Arg Phe Ser Gly Ser Gly Ser Gly Thr Asp Phe Thr Leu
 65                  70                  75                  80

```
Thr Ile Ser Ser Leu Gln Ala Glu Asp Val Ala Val Tyr Tyr Cys Gln
                85                  90                  95

Gln Tyr Tyr Ser Thr Pro Leu Thr Phe Gly Gly Gly Thr Lys Leu Glu
            100                 105                 110

Ile Lys

<210> SEQ ID NO 11
<211> LENGTH: 115
<212> TYPE: PRT
<213> ORGANISM: Homo sapiens
<220> FEATURE:
<221> NAME/KEY: CHAIN
<222> LOCATION: (1)...(115)
<223> OTHER INFORMATION: heavy chain germline donor

<400> SEQUENCE: 11

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Glu Tyr Phe Gln His Trp Gly Gln Gly Thr Leu Val Thr
            100                 105                 110

Val Ser Ser
        115

<210> SEQ ID NO 12
<211> LENGTH: 115
<212> TYPE: PRT
<213> ORGANISM: Homo sapiens
<220> FEATURE:
<221> NAME/KEY: CHAIN
<222> LOCATION: (1)...(115)
<223> OTHER INFORMATION: heavy chain rearranged donor

<400> SEQUENCE: 12

Gln Val Gln Leu Val Glu Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ala Val Ala Gly Trp Gly Gln Gly Thr Leu Val Thr
            100                 105                 110

Val Ser Ser
```

<210> SEQ ID NO 13
<211> LENGTH: 113
<212> TYPE: PRT
<213> ORGANISM: Artificial Sequence
<220> FEATURE:
<223> OTHER INFORMATION: synthetically constructed consensus identity
<220> FEATURE:
<221> NAME/KEY: misc_feature
<222> LOCATION: (1)...(113)
<223> OTHER INFORMATION: Xaa = any amino acid

<400> SEQUENCE: 13

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Xaa Leu Xaa Ser
            20                  25                  30

Ser Asn Xaa Lys Xaa Tyr Leu Ala Trp Tyr Gln Gln Lys Pro Gly Gln
        35                  40                  45

Pro Pro Lys Leu Leu Ile Tyr Xaa Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Xaa Tyr Ser Thr Pro Xaa Thr Phe Gly Gly Gly Thr Lys Leu Glu Ile
                100                 105                 110

Lys

<210> SEQ ID NO 14
<211> LENGTH: 113
<212> TYPE: PRT
<213> ORGANISM: Homo sapiens
<220> FEATURE:
<221> NAME/KEY: CHAIN
<222> LOCATION: (1)...(113)
<223> OTHER INFORMATION: VK germline donor

<400> SEQUENCE: 14

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Asn Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
                100                 105                 110

Lys

<210> SEQ ID NO 15
<211> LENGTH: 113
<212> TYPE: PRT
<213> ORGANISM: Homo sapiens

```
<220> FEATURE:
<221> NAME/KEY: CHAIN
<222> LOCATION: (1)...(113)
<223> OTHER INFORMATION: VK rearranged donor

<400> SEQUENCE: 15
```

Asp Ile Val Met Thr Gln Ser Pro Asp Ser Leu Ala Val Ser Leu Gly
 1               5                   10                  15

Glu Arg Ala Thr Ile Asn Cys Lys Ser Ser Gln Ser Val Leu Tyr Ser
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Asn Ala Ser Thr Arg Glu Ser Gly Val
     50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                 85                  90                  95

Tyr Tyr Ser Thr Pro Leu Thr Phe Gly Gly Gly Thr Lys Leu Glu Ile
            100                 105                 110

Lys

```
<210> SEQ ID NO 16
<211> LENGTH: 113
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(113)
<223> OTHER INFORMATION: hRP215_VK2

<400> SEQUENCE: 16
```

Asp Ile Val Met Thr Gln Ser Pro Asp Ser Leu Ala Val Ser Leu Gly
 1               5                   10                  15

Glu Arg Ala Thr Ile Asn Cys Lys Ser Ser Gln Ser Leu Leu Asn Ser
             20                  25                  30

Ser Asn Gln Lys Ser Tyr Leu Ala Trp Tyr Gln Gln Lys Pro Gly Gln
         35                  40                  45

Pro Pro Lys Leu Leu Ile Tyr Phe Ala Ser Thr Arg Glu Ser Gly Val
     50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                 85                  90                  95

His Tyr Ser Thr Pro Ser Thr Phe Gly Gly Gly Thr Lys Leu Glu Ile
            100                 105                 110

Lys

```
<210> SEQ ID NO 17
<211> LENGTH: 113
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(113)
<223> OTHER INFORMATION: hRP215_VK3
```

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ser Asn Gln Lys Ser Tyr Leu Ala Trp Tyr Gln Gln Lys Pro Gly Gln
        35                  40                  45

Pro Pro Lys Leu Leu Val Tyr Phe Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

His Tyr Ser Thr Pro Ser Thr Phe Gly Gly Gly Thr Lys Leu Glu Ile
            100                 105                 110

Lys

<210> SEQ ID NO 18
<211> LENGTH: 112
<212> TYPE: PRT
<213> ORGANISM: Artificial Sequence
<220> FEATURE:
<223> OTHER INFORMATION: synthetically constructed consensus identity
<220> FEATURE:
<221> NAME/KEY: misc_feature
<222> LOCATION: (1)...(112)
<223> OTHER INFORMATION: Xaa = any amino acid

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Met His Trp Val Phe Gln Ala Pro Gly Gln Gly Leu Glu Trp Met
        35                  40                  45

Gly Xaa Ile Asp Thr Ser Asp Ser Tyr Thr Arg Tyr Ala Gln Lys Phe
50                  55                  60

Gln Gly Arg Val Thr Xaa Thr Xaa Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Trp Gly Gln Gly Thr Leu Val Thr Val Ser
            100                 105                 110

<210> SEQ ID NO 19
<211> LENGTH: 115
<212> TYPE: PRT
<213> ORGANISM: Homo sapiens
<220> FEATURE:
<221> NAME/KEY: CHAIN
<222> LOCATION: (1)...(115)
<223> OTHER INFORMATION: VH germline donor

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Phe Gln Ala Pro Gly Gln Gly Leu Glu Trp Met

```
                35                  40                  45
Gly Ile Ile Asp Thr Ser Gly Ser Thr Tyr Ala Gln Lys Phe
        50                  55                  60
Gln Gly Arg Val Thr Met Thr Arg Asp Thr Ser Thr Val Tyr
 65                  70                  75                  80
Met Glu Leu Ser Ser Leu Arg Ser Glu Asp Thr Ala Val Tyr Tyr Cys
                85                  90                  95
Ala Arg Ala Glu Tyr Phe Gln His Trp Gly Gln Gly Thr Leu Val Thr
            100                 105                 110
Val Ser Ser
        115

<210> SEQ ID NO 20
<211> LENGTH: 115
<212> TYPE: PRT
<213> ORGANISM: Homo sapiens
<220> FEATURE:
<221> NAME/KEY: CHAIN
<222> LOCATION: (1)...(115)
<223> OTHER INFORMATION: VH rearranged donor

<400> SEQUENCE: 20

Gln Val Gln Leu Val Glu Ser Gly Ala Glu Val Lys Lys Pro Gly Ala
 1               5                  10                  15
Ser Val Lys Val Ser Cys Lys Ala Ser Gly Tyr Thr Phe Thr Ser Tyr
                20                  25                  30
Ala Met His Trp Val Phe Gln Ala Pro Gly Gln Gly Leu Glu Trp Met
                35                  40                  45
Gly Gly Ile Asn Thr Ile Phe Gly Thr Ala Asn Tyr Ala Gln Lys Phe
        50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                85                  90                  95
Ala Arg Gly Ala Ala Val Ala Gly Trp Gly Gln Gly Thr Leu Val Thr
            100                 105                 110
Val Ser Ser
        115

<210> SEQ ID NO 21
<211> LENGTH: 113
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(113)
<223> OTHER INFORMATION: hRP215_VH1

<400> SEQUENCE: 21

Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Ser Tyr
                20                  25                  30
Trp Ile Asn Trp Val Phe Gln Ala Pro Gly Gln Gly Leu Glu Trp Met
                35                  40                  45
Gly Ala Ile Ile Thr Ser Asp Ser Tyr Thr Arg Tyr Ala Gln Lys Phe
        50                  55                  60
```

```
Gln Gly Arg Val Thr Met Thr Val Asp Glu Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Trp Gly Gln Gly Thr Leu Val Thr Val Ser
            100                 105                 110

Ser

<210> SEQ ID NO 22
<211> LENGTH: 113
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(113)
<223> OTHER INFORMATION: hRP215_VH2

<400> SEQUENCE: 22

Gln Val Gln Leu Val Glu Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Trp Met His Trp Val Phe Gln Ala Pro Gly Gln Gly Leu Glu Trp Met
             35                  40                  45

Gly Gly Ile Asp Thr Ser Asp Ser Tyr Thr Arg Tyr Ala Gln Lys Phe
     50                  55                  60

Gln Gly Arg Val Thr Leu Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Trp Gly Gln Gly Thr Leu Val Thr Val Ser
            100                 105                 110

Ser

<210> SEQ ID NO 23
<211> LENGTH: 113
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(113)
<223> OTHER INFORMATION: hRP215_VH3

<400> SEQUENCE: 23

Gln Val Gln Leu Val Glu Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Trp Met His Trp Val Phe Gln Ala Pro Gly Gln Gly Leu Glu Trp Ile
             35                  40                  45

Gly Ala Ile Asp Thr Ser Asp Ser Tyr Thr Arg Tyr Ala Gln Lys Phe
     50                  55                  60

Gln Gly Arg Val Thr Leu Thr Val Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

```
Ala Arg Ser Ile Tyr Asp Trp Gly Gln Gly Thr Leu Val Thr Val Ser
            100                 105                 110

Ser

<210> SEQ ID NO 24
<211> LENGTH: 113
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(113)
<223> OTHER INFORMATION: hRP215_VH1 heavy chain

<400> SEQUENCE: 24

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
             20                  25                  30

Trp Met His Trp Val Arg Gln Ala Pro Gly Gln Gly Leu Glu Trp Met
         35                  40                  45

Gly Ala Ile Asp Thr Ser Asp Ser Tyr Thr Arg Tyr Ala Gln Lys Phe
     50                  55                  60

Gln Gly Arg Val Thr Met Thr Val Asp Glu Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Trp Gly Gln Gly Thr Leu Val Thr Val Ser
            100                 105                 110

Ser

<210> SEQ ID NO 25
<211> LENGTH: 113
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(113)
<223> OTHER INFORMATION: hRP215_VH2 heavy chain

<400> SEQUENCE: 25

Gln Val Gln Leu Val Glu Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
             20                  25                  30

Trp Met His Trp Val Arg Gln Ala Pro Gly Gln Gly Leu Glu Trp Met
         35                  40                  45

Gly Gly Ile Asp Thr Ser Asp Ser Tyr Thr Arg Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Trp Gly Gln Gly Thr Leu Val Thr Val Ser
            100                 105                 110

Ser
```

<210> SEQ ID NO 26
<211> LENGTH: 113
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(113)
<223> OTHER INFORMATION: hRP215_VH3 heavy chain

<400> SEQUENCE: 26

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
            20                  25                  30

Trp Met His Trp Val Arg Gln Ala Pro Gly Gln Gly Leu Glu Trp Ile
        35                  40                  45

Gly Ala Ile Asp Thr Ser Asp Ser Tyr Thr Arg Tyr Ala Gln Lys Phe
    50                  55                  60

Gln Gly Arg Val Thr Leu Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Trp Gly Gln Gly Thr Leu Val Thr Val Ser
            100                 105                 110

Ser
```

<210> SEQ ID NO 27
<211> LENGTH: 113
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(113)
<223> OTHER INFORMATION: RP215_murine heavy chain

<400> SEQUENCE: 27

```
Gln Val Gln Leu Gln Gln Pro Gly Ala Glu Leu Val Met Pro Gly Ala
 1               5                  10                  15

Ser Val Lys Met Ser Cys Lys Ala Ser Gly Tyr Thr Phe Thr Asp Tyr
            20                  25                  30

Trp Met His Trp Val Lys Gln Arg Pro Gly Gln Gly Leu Glu Trp Ile
        35                  40                  45

Gly Ala Ile Asp Thr Ser Asp Ser Tyr Thr Arg Tyr Asn Gln Lys Phe
    50                  55                  60

Lys Asp Lys Ala Thr Leu Thr Val Asp Glu Ser Ser Ser Thr Ala Phe
65                  70                  75                  80

Met Gln Leu Ser Ser Leu Thr Ser Glu Asp Ser Ala Val Tyr Tyr Cys
                85                  90                  95

Ala Arg Ser Ile Tyr Asp Trp Gly Gln Gly Thr Leu Val Thr Val Ser
            100                 105                 110

Ala
```

<210> SEQ ID NO 28
<211> LENGTH: 113
<212> TYPE: PRT

-continued

```
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(113)
<223> OTHER INFORMATION: hRP215_VL1 light chain

<400> SEQUENCE: 28
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ser Asn Gln Lys Ser Tyr Leu Ala Trp Tyr Gln Gln Lys Pro Gly Gln
        35                  40                  45

Pro Pro Lys Leu Leu Ile Tyr Phe Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Ser Thr Pro Ser Thr Phe Gly Gly Gly Thr Lys Leu Glu Ile
            100                 105                 110

Lys

```
<210> SEQ ID NO 29
<211> LENGTH: 113
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(113)
<223> OTHER INFORMATION: hRP215_VL2 light chain

<400> SEQUENCE: 29
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ser Asn Gln Lys Ser Tyr Leu Ala Trp Tyr Gln Gln Lys Pro Gly Gln
        35                  40                  45

Pro Pro Lys Leu Leu Val Tyr Phe Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

His Tyr Ser Thr Pro Ser Thr Phe Gly Gly Gly Thr Lys Leu Glu Ile
            100                 105                 110

Lys

```
<210> SEQ ID NO 30
<211> LENGTH: 113
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
```

```
<222> LOCATION: (1)...(113)
<223> OTHER INFORMATION: RP215_murine light chain

<400> SEQUENCE: 30

Asp Ile Val Met Thr Gln Ser Pro Ser Ser Leu Ala Met Ser Val Gly
 1               5                   10                  15

Gln Lys Val Thr Met Ser Cys Lys Ser Ser Gln Ser Leu Leu Asn Ser
            20                  25                  30

Ser Asn Gln Lys Ser Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Ser Thr Phe Gly Gly Gly Thr Lys Leu Glu Ile
            100                 105                 110

Lys

<210> SEQ ID NO 31
<211> LENGTH: 1416
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(1416)
<223> OTHER INFORMATION: DNA sequence encoding hRP215_VH1 - H0021

<400> SEQUENCE: 31
atggagaccg acaccctgct gctctgggtg ctgctgctct gggtgcccgg ctccaccgga      60
caggtgcagc ttgttcagag tggcgccgaa gtgaagaagc caggcgcttc cgtgaaggtg     120
agctgcaagg catcaggcta caccttcact gattattgga tgcactgggt gagacaggca     180
cccggtcagg ggctcgaatg gatgggcgcc atcgatacta gcgattccta taccagatac     240
gcacagaagt ttcagggaag agttaccatg actgtcgatg aatctacaag caccgtctac     300
atggagctga gcagcctgcg gtctgaggac ccgctgtttt actactgtgc ccgctccatc     360
tatgattggg gtcaaggaac cttggtcaca gtgagttctg ctagcaccaa gggcccccagc     420 gtgttccctc tggcccccag cagcaagagc accagcggcg gaaccgccgc cctgggctgc     480
ctggtgaagg actacttccc cgagcccgtg accgtgtcct ggaacagcgg cgctctgacc     540
agcggagtgc acaccttccc tgccgtgctg cagagcagcg gcctgtactc cctgagcagc     600
gtggtgaccg tgcccagcag cagcctgggc acccagacct acatctgcaa cgtgaaccac     660
aagccctcca acaccaaggt ggacaagaag gtggagccta agagctgcga caagacccac     720
acctgccctc cctgccccgc ccccgagctg ctgggcggac ccagcgtgtt cctgttccct     780
cccaagccca aggacaccct gatgatcagc cgcacccccg aggtgacctg cgtggtggtg     840
gacgtgagcc acgaggaccc cgaggtgaag ttcaactggt acgtggacgg cgtggaggtg     900
cacaacgcca agaccaagcc tcgggaggag cagtacaact ccacctaccg cgtggtgagc     960
gtgctgaccg tgctgcacca ggactggctg aacggcaagg agtacaagtg caaggtgagc    1020
aacaaggccc tgcccgctcc catcgagaag accatcagca ggccaagggg ccagccccgg    1080
gagcctcagg tgtacaccct gcccccccagc cgcgacgagc tgaccaagaa ccaggtgagc    1140
```

| ctgacctgcc tggtgaaggg cttctacccc tccgacatcg ccgtggagtg ggagagcaac | 1200 |
| ggccagcctg agaacaacta caagaccacc cctcccgtgc tggacagcga cggcagcttc | 1260 |
| ttcctgtaca gcaagctgac cgtggacaag tcccggtggc agcagggcaa cgtgttcagc | 1320 |
| tgcagcgtga tgcacgaggc cctgcacaac cactacaccc agaagagcct gagcctgagc | 1380 |
| cccggaaagg attacaagga cgacgatgac aagtag | 1416 |

<210> SEQ ID NO 32
<211> LENGTH: 1416
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(1416)
<223> OTHER INFORMATION: DNA sequence encoding hRP215_VH2 - H0022

<400> SEQUENCE: 32

| atggagaccg acaccctgct gctctgggtg ctgctgctct gggtgcccgg ctccaccgga | 60 |
| caggtgcagc ttgttgagag tggcgccgaa gtgaagaagc caggcgcttc cgtgaaggtg | 120 |
| agctgcaagg catcaggcta caccttcact gattattgga tgcactgggt gagacaggca | 180 |
| cccggtcagg ggctcgaatg gatgggcggc atcgatacta gcgattccta taccagatac | 240 |
| gcacagaagt ttcagggaag agttaccatc actgccgatg aatctacaag caccgcctac | 300 |
| atggagctga gcagcctgcg gtctgaggac accgctgttt actactgtgc ccgctccatc | 360 |
| tatgattggg gtcaaggaac cttggtcaca gtgagttctg ctagcaccaa gggccccagc | 420 |
| gtgttccctc tggcccccag cagcaagagc accagcggcg gaaccgccgc cctgggctgc | 480 |
| ctggtgaagg actacttccc cgagcccgtg accgtgtcct ggaacagcgg cgctctgacc | 540 |
| agcggagtgc acaccttccc tgccgtgctg cagagcagcg gcctgtactc cctgagcagc | 600 |
| gtggtgaccg tgcccagcag cagcctgggc acccagacct acatctgcaa cgtgaaccac | 660 |
| aagccctcca cacccaaggt ggacaagaag gtggagccta agagctgcga caagacccac | 720 |
| acctgccctc cctgccccgc ccccgagctg ctgggcggac ccagcgtgtt cctgttccct | 780 |
| cccaagccca aggacaccct gatgatcagc cgcacccccg aggtgacctg cgtggtggtg | 840 |
| gacgtgagcc acgaggaccc cgaggtgaag ttcaactggt acgtggacgg cgtggaggtg | 900 |
| cacaacgcca agaccaagcc tcgggaggag cagtacaact ccacctaccg cgtggtgagc | 960 |
| gtgctgaccg tgctgcacca ggactggctg aacggcaagg agtacaagtg caaggtgagc | 1020 |
| aacaaggccc tgcccgctcc catcgagaag accatcagca aggccaaggg ccagccccgg | 1080 |
| gagcctcagg tgtacaccct gccccccagc cgcgacgagc tgaccaagaa ccaggtgagc | 1140 |
| ctgacctgcc tggtgaaggg cttctacccc tccgacatcg ccgtggagtg ggagagcaac | 1200 |
| ggccagcctg agaacaacta caagaccacc cctcccgtgc tggacagcga cggcagcttc | 1260 |
| ttcctgtaca gcaagctgac cgtggacaag tcccggtggc agcagggcaa cgtgttcagc | 1320 |
| tgcagcgtga tgcacgaggc cctgcacaac cactacaccc agaagagcct gagcctgagc | 1380 |
| cccggaaagg attacaagga cgacgatgac aagtag | 1416 |

<210> SEQ ID NO 33
<211> LENGTH: 1416
<212> TYPE: DNA
<213> ORGANISM: Artificial Sequence
<220> FEATURE:

<223> OTHER INFORMATION: synthetic construct
<220> FEATURE:
<221> NAME/KEY: misc_feature
<222> LOCATION: (1)...(1416)
<223> OTHER INFORMATION: DNA sequence encoding hRP215_VH3 - H0023

<400> SEQUENCE: 33

| | | |
|---|---|---|
| atggagaccg acaccctgct gctctgggtg ctgctgctct gggtgcccgg ctccaccgga | 60 |
| caggtgcagc ttgttcagag tggcgccgaa gtgaagaagc caggcgcttc cgtgaaggtg | 120 |
| agctgcaagg catcaggcta caccttcact gattattgga tgcactgggt gagacaggca | 180 |
| cccggtcagg ggctcgaatg gatgggcgcc atcgatacta gcgattccta taccagatac | 240 |
| gcacagaagt ttcagggaag agttaccctg actgtcgatg aatctacaag caccgtctac | 300 |
| atggagctga gcagcctgcg gtctgaggac accgctgttt actactgtgc ccgctccatc | 360 |
| tatgattggg gtcaaggaac cttggtcaca gtgagttctg ctagcaccaa gggccccagc | 420 |
| gtgttccctc tggcccccag cagcaagagc ccagcggcg aaccgccgc cctgggctgc | 480 |
| ctggtgaagg actacttccc cgagcccgtg accgtgtcct ggaacagcgg cgctctgacc | 540 |
| agcggagtgc acaccttccc tgccgtgctg cagagcagcg gcctgtactc cctgagcagc | 600 |
| gtggtgaccg tgcccagcag cagcctgggc acccagacct acatctgcaa cgtgaaccac | 660 |
| aagccctcca acaccaaggt ggacaagaag gtggagccta agagctgcga caagacccac | 720 |
| acctgccctc cctgccccgc ccccgagctg ctgggcggac ccagcgtgtt cctgttccct | 780 |
| cccaagccca aggacaccct gatgatcagc cgcacccccg aggtgacctg cgtggtggtg | 840 |
| gacgtgagcc acgaggaccc cgaggtgaag ttcaactggt acgtggacgg cgtggaggtg | 900 |
| cacaacgcca agaccaagcc tcgggaggag cagtacaact ccacctaccg cgtggtgagc | 960 |
| gtgctgaccg tgctgcacca ggactggctg aacggcaagg agtacaagtg caaggtgagc | 1020 |
| aacaaggccc tgcccgctcc catcgagaag accatcagca aggccaaggg ccagccccgg | 1080 |
| gagcctcagg tgtacaccct gcccccagc cgcgacgagc tgaccaagaa ccaggtgagc | 1140 |
| ctgacctgcc tggtgaaggg cttctacccc tccgacatcg ccgtggagtg ggagagcaac | 1200 |
| ggccagcctg agaacaacta caagaccacc cctcccgtgc tggacagcga cggcagcttc | 1260 |
| ttcctgtaca gcaagctgac cgtggacaag tcccggtggc agcagggcaa cgtgttcagc | 1320 |
| tgcagcgtga tgcacgaggc cctgcacaac cactacaccc agaagagcct gagcctgagc | 1380 |
| cccggaaagg attacaagga cgacgatgac aagtag | 1416 |

<210> SEQ ID NO 34
<211> LENGTH: 723
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(723)
<223> OTHER INFORMATION: DNA sequence encoding hRP215_VL1 - L0022

<400> SEQUENCE: 34

| | | |
|---|---|---|
| atggagaccg acaccctgct gctctgggtg ctgctgctct gggtgcccgg ctccaccgga | 60 |
| gatatcgtga tgacccagtc ccccgacagc ctggccgtct ctctgggtga gcgggcaacc | 120 |
| atcaactgta gtctagcca gtccctgttg aacagtagca tcaaaagag ctatcttgcc | 180 |
| tggtatcagc aaaagcctgg ccagccacca aaactgctta tctatttcgc ttccactcgg | 240 |
| gaaagcggtg taccagaccg cttttctggc tcaggttccg gcacagactt taccttgacc | 300 |

-continued

```
attagctccc ttcaggcaga ggacgtggca gtctactatt gccagcaaca ctactccact      360
ccatcaacct ttggaggtgg cacaaaactg gagattaagc ggaccgtggc cgcccccagc      420
gtgttcatct tccctcccag cgacgagcag ctgaagtctg gcaccgccag cgtggtgtgc      480
ctgctgaaca acttctaccc ccgcgaggcc aaggtgcagt ggaaggtgga caacgccctg      540
cagagcggca acagccagga gagcgtgacc gagcaggact ccaaggacag cacctacagc      600
ctgagcagca ccctgaccct gagcaaggcc gactacgaga agcacaaggt gtacgcctgc      660
gaggtgaccc caccagggact gtctagcccc gtgaccaaga gcttcaaccg gggcgagtgc      720
taa                                                                   723

<210> SEQ ID NO 35
<211> LENGTH: 723
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(723)
<223> OTHER INFORMATION: DNA sequence encoding hRP215_VL2 - L0023

<400> SEQUENCE: 35
atggagaccg acaccctgct gctctgggtg ctgctgctct gggtgcccgg ctccaccgga       60
gatatcgtga tgacccagtc ccccgacagc ctggccgtct ctctgggtga gcgggcaacc      120
atcaactgta agtctagcca gtccctgttg aacagtagca atcaaaagag ctatcttgcc      180
tggtatcagc aaaagcctgg ccagccacca aaactgcttg tctatttcgc ttccactcgg      240
gaaagcggtg taccagaccg ctttctggc tcaggttccg gcacagactt taccttgacc       300
attagctccc ttcaggcaga ggacgtggca gtctactttt gccagcaaca ctactccact      360
ccatcaacct ttggaggtgg cacaaaactg gagattaagc ggaccgtggc cgcccccagc      420
gtgttcatct tccctcccag cgacgagcag ctgaagtctg gcaccgccag cgtggtgtgc      480
ctgctgaaca acttctaccc ccgcgaggcc aaggtgcagt ggaaggtgga caacgccctg      540
cagagcggca acagccagga gagcgtgacc gagcaggact ccaaggacag cacctacagc      600
ctgagcagca ccctgaccct gagcaaggcc gactacgaga agcacaaggt gtacgcctgc      660
gaggtgaccc caccagggact gtctagcccc gtgaccaaga gcttcaaccg gggcgagtgc      720
taa                                                                   723
```